US 6,581,595 B1

(12) United States Patent
Murdock et al.

(10) Patent No.: US 6,581,595 B1
(45) Date of Patent: Jun. 24, 2003

(54) POSITIVE AIRWAY PRESSURE DEVICE WITH INDIRECT CALORIMETRY SYSTEM

(75) Inventors: Larry R. Murdock, Alta Loma, CA (US); William B. Ross, Mission Viejo, CA (US)

(73) Assignee: Sensormedics Corporation, Yorba Linda, CA (US)

( * ) Notice: Subject to any disclaimer, the term of this patent is extended or adjusted under 35 U.S.C. 154(b) by 178 days.

(21) Appl. No.: 09/713,748

(22) Filed: Nov. 14, 2000

(51) Int. Cl.[7] .......................... A61M 16/00; A61B 5/08

(52) U.S. Cl. ........................ 128/204.18; 128/204.23; 600/531

(58) Field of Search .......... 128/204.18, 204.21–204.23, 128/204.26, 204.29, 205.11, 205.18, 205.23, 205.24; 600/529, 530, 531, 532, 533–538

(56) References Cited

U.S. PATENT DOCUMENTS

| | | | | |
|---|---|---|---|---|
| 3,507,146 A | * | 4/1970 | Webb | 73/31.04 |
| 4,197,858 A | * | 4/1980 | Osborn | 600/531 |
| 4,457,310 A | * | 7/1984 | Swyer et al. | 600/481 |
| 4,572,208 A | * | 2/1986 | Cutler et al. | 600/531 |
| 4,619,269 A | * | 10/1986 | Cutler et al. | 128/204.16 |
| 4,763,664 A | * | 8/1988 | Merilainen | 128/201.23 |
| 4,832,042 A | * | 5/1989 | Poppendiek et al. | 128/205.19 |
| 4,917,108 A | * | 4/1990 | Mault | 128/204.22 |
| 5,038,792 A | * | 8/1991 | Mault | 600/531 |
| 5,072,737 A | * | 12/1991 | Goulding | 600/531 |
| 5,117,674 A | * | 6/1992 | Howard | 600/531 |
| 5,178,155 A | * | 1/1993 | Mault | 600/531 |
| 5,179,958 A | * | 1/1993 | Mault | 300/531 |
| 5,363,857 A | * | 11/1994 | Howard | 600/531 |
| 5,611,348 A | * | 3/1997 | Merilainen | 422/84 |
| 5,705,735 A | * | 1/1998 | Acorn | 128/204.23 |
| 5,836,300 A | * | 11/1998 | Mault | 128/204.23 |
| 5,868,133 A | * | 2/1999 | DeVries et al. | 128/204.18 |
| 5,957,127 A | * | 9/1999 | Yamamori et al. | 128/204.22 |
| 6,135,107 A | * | 10/2000 | Mault | 128/204.23 |
| 6,277,645 B1 | * | 8/2001 | Mault | 422/84 |
| 6,309,360 B1 | * | 10/2001 | Mault | 600/531 |
| 6,315,719 B1 | * | 11/2001 | Rode et al. | 600/300 |
| 6,325,978 B1 | * | 12/2001 | Labuda et al. | 422/84 |
| 6,349,724 B1 | * | 2/2002 | Burton et al. | 128/204.18 |

(List continued on next page.)

OTHER PUBLICATIONS

The Vmax Series, SensorMedics, Yorba Linda, California downloaded from http://www.sensormedics.com/Products/Diagnostics/products_vmax.htm May 30, 2000.

SensorMedics Vmax Series Model Descriptions, SensorMedics, Yorba Linda, California downloaded from http://www.sensormedics.com/Products/Diagnostics/products_vmax_descr.htm May 30, 2000.

Alura Nasal CPAP System, SensorMedics, Yorba Linda, California downloaded from http://www.sensormedics.com/Products/Diagnostics/Products_Alura.htm May 30, 2000.

Primary Examiner—Weilun Lo
Assistant Examiner—Teena Mitchell
(74) Attorney, Agent, or Firm—Sidley Austin Brown & Wood LLP

(57) ABSTRACT

A device and method for applying positive airway pressure to a patient includes an indirect calorimetry system for measuring a patient's resting energy expenditure (REE). The device includes a breathing circuit, one end of which includes a patient interface device such as a nasal face mask. A bi-directional pump is positioned within the breathing circuit. The bi-directional pump pumps gas in a first direction during the application of positive airway pressure. The bi-directional pump reverses direction when the device is in the indirect calorimetry mode. In this IC mode, patient's expired gases are diluted and passed through an IC module containing an oxygen sensor, a carbon dioxide sensor, and a flow rate sensor. The device includes a microprocessor for calculating the patient's REE based on the measured oxygen concentration, carbon dioxide concentration, and flow rate.

20 Claims, 3 Drawing Sheets

U.S. PATENT DOCUMENTS

| | | | |
|---|---|---|---|
| 6,358,215 B1 * | 3/2002 | Ricciardelli | 250/339.06 |
| 6,402,698 B1 * | 6/2002 | Mault | 600/531 |
| 6,475,158 B1 * | 11/2002 | Orr et al. | 600/531 |
| 6,488,635 B1 * | 12/2002 | Mottram | 600/551 |
| 6,506,608 B2 * | 1/2003 | Mault | 436/133 |
| 2001/0029340 A1 * | 10/2001 | Mault et al. | 600/532 |
| 2002/0095096 A1 * | 7/2002 | Mault | 600/531 |
| 2002/0173728 A1 * | 11/2002 | Mault | 600/531 |

\* cited by examiner

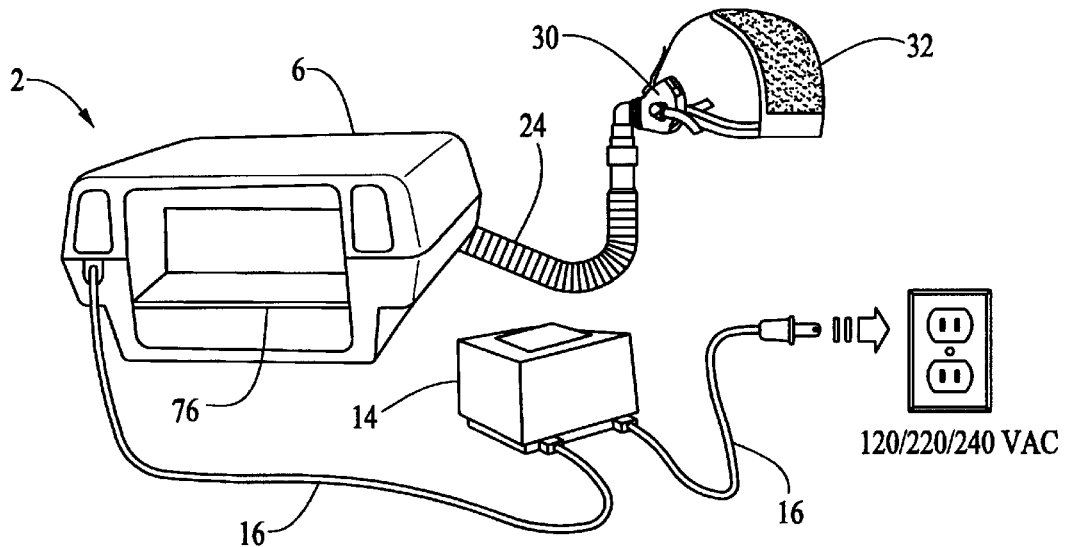
fig.2
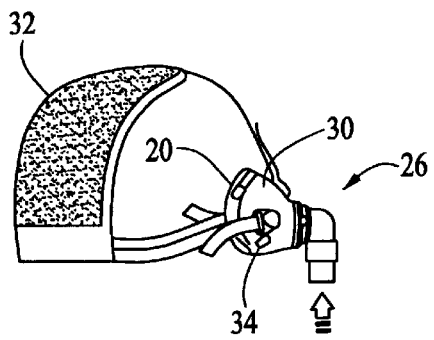
fig.3
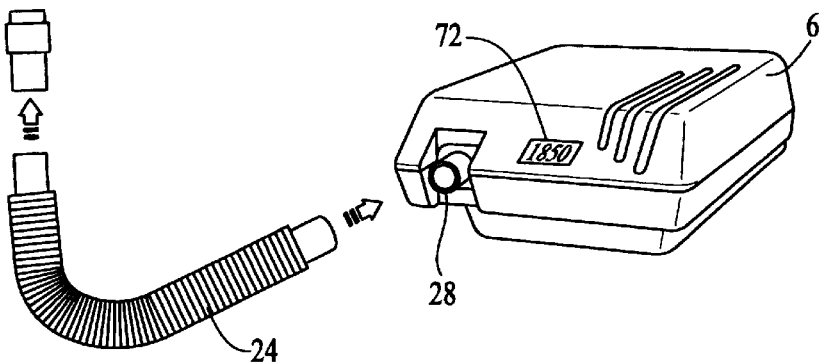

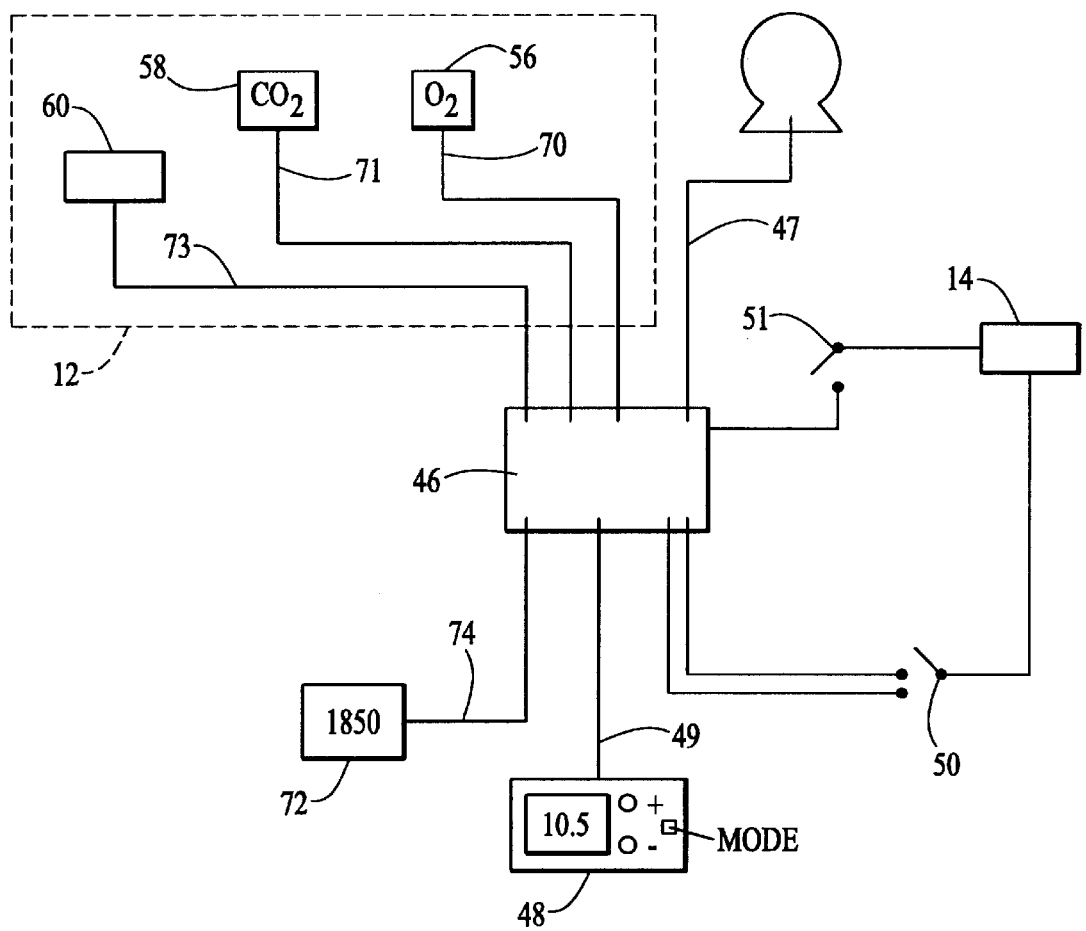

POSITIVE AIRWAY PRESSURE DEVICE WITH INDIRECT CALORIMETRY SYSTEM

BACKGROUND OF THE INVENTION

The field of the invention relates generally to devices for the treatment of Obstructive Sleep Apnea (OSA). More specifically, the invention relates to devices and methods for the treatment and resolution of the underlying obesity that causes, exacerbates, or triggers OSA. The device and methods employ objective monitoring of the metabolic rate of a patient.

Sleep related breathing disorders adversely affect an individual's breathing during periods of sleep. Breathing disruption in sleep often results from the collapse or closing of an individual's air passageway. OSA, as one common example of a sleep related breathing disorder, is an abnormal physical condition that affects a person's ability to breathe properly after falling asleep. Persons suffering from sleep apnea can stop breathing for periods as short as a few seconds and as long as a few minutes.

Frequently, a patient that suffers from OSA is obese. Obesity contributes to an increase in the upper airway resistance due to deposits of adipose tissue in the upper airway, specifically, the hypopharynx. During periods of sleep, tissue in this region relaxes and blocks airflow into and out of the afflicted person's lungs.

Typically, sleep related breathing disorders such as OSA are treated by Continuous Positive Air Pressure (CPAP) therapy. In CPAP therapy, a device that is essentially an air pump forces air into an individual's air passageway. The CPAP device maintains sufficient pressure to keep the air passageway open during periods of sleep. The patient typically wears a masklike device that is connected to the CPAP device to provide an elevated air pressure in the patient's upper air passageway. One such device is the ALURA Nasal CPAP System sold by Thermo Respiratory Group/Bird SensorMedics Bear, 1100 Bird Center Drive, Palm Springs, Calif. 92262. Other devices known as BiPAP (Bi-Level Positive Airway Pressure) devices operate at two positive air pressure levels. A lower pressure level is used during exhalation while a higher pressure level is used during inhalation. The BiPAP device makes it easier to exhale due to the lower pressure used during exhalation. BiPAP devices are often prescribed for individuals that require higher pressures than those present in CPAP devices.

Since OSA is so often associated with obesity, it is desirable to treat the underlying obesity condition. Generally, obesity may be resolved by the strict application of nutrition and diet control. It has been demonstrated, for example, that the measurement of resting energy expenditure (REE) by indirect calorimetry (IC) is useful in determining an individual patient's caloric needs and monitoring the patient's nutritional intake.

At the present time, there does not exist a comprehensive device that can monitor a patient's REE that also delivers positive airway pressure (CPAP or BiPAP). A device combining these two functions has been elusive since there is a natural clash between the positive airflow of CPAP/BiPAP devices and the negative airflow requirement of IC devices. Accordingly, there is a need for a single device that can (1) provide positive airway pressure to a patient, and (2) monitor or measure the REE of the patient.

SUMMARY OF THE INVENTION

In a first aspect of the invention, a device for applying positive airway pressure to a patient and measuring the patient's resting energy expenditure includes a breathing circuit having a first end and a second end. A patient interface device is coupled to one of the first and second ends. A bi-directional pump is positioned within the breathing circuit between the first end and the second end. An indirect calorimetry module is positioned within the breathing circuit. The indirect calorimetry module measures the patient's resting energy expenditure.

In a second aspect of the invention, a device for applying positive airway pressure to a patient and measuring the patient's resting energy expenditure includes a breathing circuit having a patient interface device connected at one end and an inlet/exhaust port at the other end of the breathing circuit. A bi-directional pump is positioned within the breathing circuit between the patient interface device and the inlet/exhaust port. An indirect calorimetry module is also positioned within the breathing circuit and adjacent to the bi-directional pump. The indirect calorimetry module includes an oxygen sensor, a carbon dioxide sensor, and a flow rate sensor. The device also includes a microprocessor for calculating the patient's resting energy expenditure based on the concentration of oxygen, the concentration or carbon dioxide, and the flow rate within breathing circuit.

In a third aspect of the invention, a method of supplying positive airway pressure to a patient includes the steps of supplying a patient with positive airway pressure via a breathing circuit, the positive airway pressure traveling through the breathing circuit in a first direction. Next, the flow in the breathing circuit is reversed during one or more expiration breaths of a patient. The concentration of oxygen and carbon dioxide is monitored in the breathing circuit during the one or more expiration breaths. The flow rate of gas in the breathing circuit is also monitored during the one or more expiration breaths. Finally, the resting energy expenditure of the patient is calculated based on the concentration of oxygen, the concentration of carbon dioxide, and the flow rate within the breathing circuit.

It is an object of the invention to provide a device that delivers positive airway pressure to a patient that also has the capability to measure REE. The device can be used in connection with a patient's weight reduction or weight maintenance program. The device gives objective feedback to the patient and/or health care provider about the patient's caloric expenditure.

BRIEF DESCRIPTION OF THE DRAWINGS

FIG. 2 illustrates a rear view of the device.

FIG. 3 illustrates a perspective view of the device including the patient circuit and the nasal face mask.

FIG. 4 illustrates schematically the electronic configuration of the microprocessor used to control the device.

FIG. 5 illustrates the underside of the device.

DETAILED DESCRIPTION OF THE PREFERRED EMBODIMENTS

Figure 1:
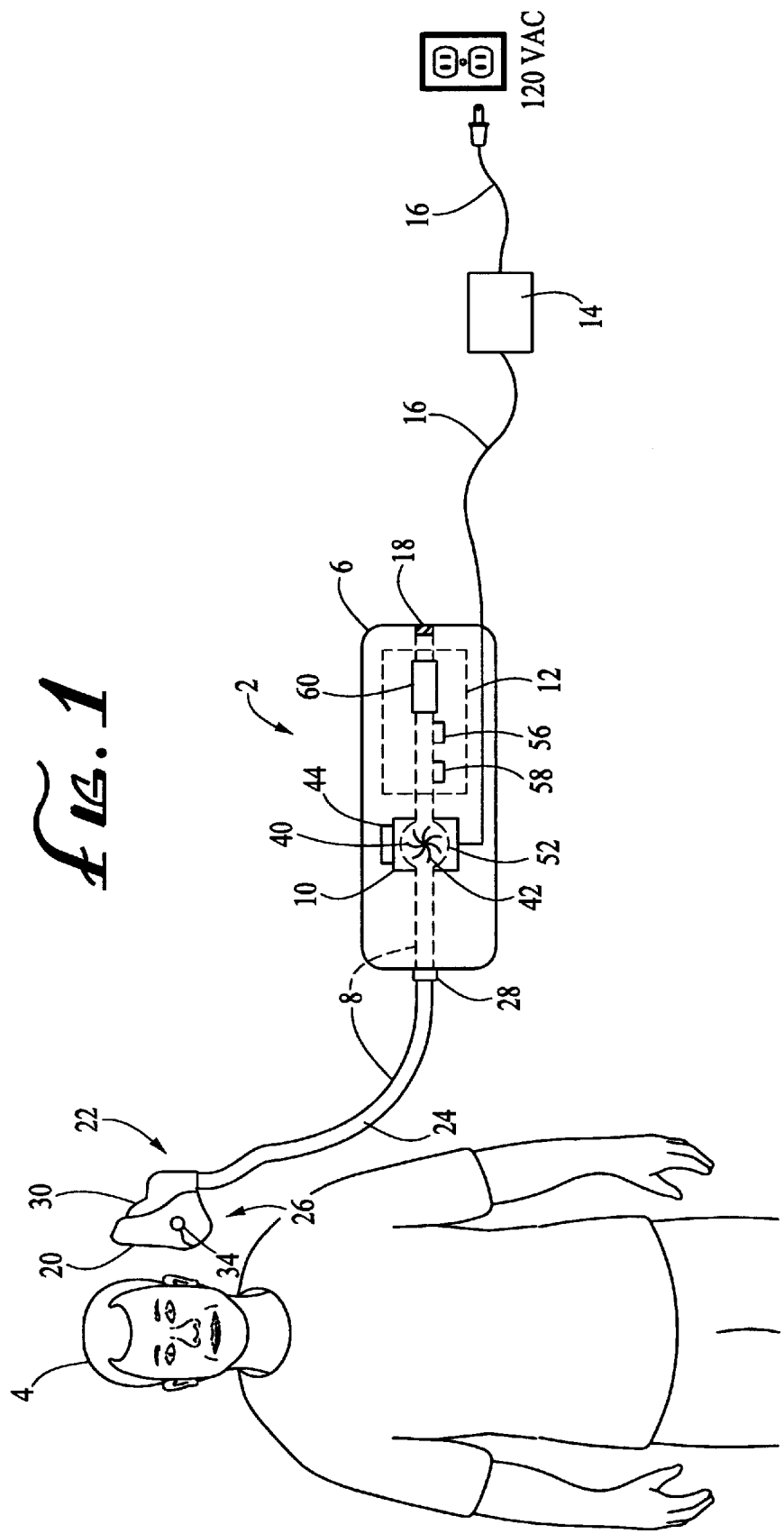
FIG. 1 schematically illustrates the combined positive airway pressure device/indirect calorimetry device.

Referring now to FIG. 1, a device 2 that includes the ability (1) to provide positive airway pressure to a patient 4 and (2) to measure the patient's 4 REE generally includes a housing 6, a breathing circuit 8 at least partially contained within the housing 6, a pump 10, and an indirect calorimetry module 12.

A power supply 14 is connected via a power cord 16 to the pump 10. The power supply 14 provides an electrical energy source to the motor 44 that drives the pump 10. The power supply 14 preferably includes a transformer therein to provide direct current (DC) to the motor 44. The power supply 14 is in turn connected to a source of alternating current (A/C). Preferably the power supply 14 is coupled to standard 120 volts alternating current (VAC) source used throughout homes and hospitals. Of course, the device 2 can also be used with non-standard.A/C sources (e.g., A/C sources in foreign countries and localities that use 220, 240 VAC and the like). In addition, the device 2 can also be powered via a dedicated DC current source such as through an automobile cigarette lighter.

The breathing circuit 8 of the device 2 generally consists of a tube or lumen-type structure that carries gas to and from the patient 4. In its most simplistic form, the breathing circuit 8 has a first end 18 and a second end 20. As seen in FIG. 1, the first end 18 is distal to the patient 4 while the second end 20 is proximal to the patient 4. The first end 18 acts as an inlet port when the device is applying positive airway pressure and acts as an exhaust port when the device 2 is run in the IC mode. It should be understood that the first end 18 and second end 20 of the breathing circuit 8 are described as first and second for purposes of illustration.

The first end 18 of the breathing circuit 8 serves as the entry point for atmospheric air into the breathing circuit 8 when the device 2 is delivering positive airway pressure to a patient 4. FIG. 2 shows the rear of the device where the first end 18 of the breathing circuit is located. The first end 18 is generally separated from the atmosphere by a removable filter 76. FIG. 3 illustrates the front end of the device 2. When the device 2 is operating in the positive airway pressure mode, the second end 20 of the breathing circuit 8 acts as the exit point for air contained within the breathing circuit 8. When the device 2 is reversed and used in the indirect calorimetry mode, the second end 20 of the breathing circuit 8 acts as the entry point for expired gases from the patient 4 while the first end 18 of the breathing circuit 8 acts as the exit point for expired gases.

Referring back to FIG. 1, the breathing circuit 8 is preferably segmented into a portion contained within the housing 6 and a patient circuit 22 external to the housing 6. The patient circuit 22 preferably includes flexible tubing 24 and a patient interface device 26. The flexible tubing 24 is connected to the breathing circuit 8 within the housing 6 via a connection point 28. The opposing end of the flexible tubing 24 is detachably engagable with the patient interface device 26. Preferably, the flexible tubing 24 is standard 22 mm tubing with ISO tapered fittings so it can be easily attached and detached to the housing 6 and patient interface device 26. The patient interface device 26 is preferably a nasal face mask 30 that is worn over the face of the patient 4. The nasal face mask 30 generally includes attachment means such as head strap 32 (as seen in FIGS. 2 and 3) or the like to affix the nasal face mask 30 to the patient 4. The nasal face mask 30 also preferably includes one or more vents 34 used to vent air into the nasal face mask 30 when the device is in the indirect calorimetry mode.

Referring back to FIG. 1, the breathing circuit 8 is preferably segmented into a portion contained within the housing 6 and a patient circuit 22 external to the housing 6. The patient circuit 22 preferably includes flexible tubing 24 and a patient interface device 26. The flexible tubing 24 is connected to the breathing circuit 8 within the housing 6 via a connection point 28. The opposing end of the flexible tubing 24 is detachably engagable with the patient interface device 26. Preferably, the flexible tubing 24 is standard 22 mm tubing with International Organization for Standardization (ISO) tapered fittings so it can be easily attached and detached to the housing 6 and patient interface device 26. The patient interface device 26 is preferably a nasal face mask 30 that is worn over the face of the patient 4. The nasal face mask 30 generally includes attachment means such as head strap 32 (as seen in FIGS. 2 and 3) or the like to affix the nasal face mask 30 to the patient 4. The nasal face mask 30 also preferably includes one or more vents 34 used to vent air into the nasal face mask 30 when the device is in the indirect calorimetry mode.

The motor 44 of the pump 10 is controlled via a microprocessor 46, as shown in FIG. 4. The microprocessor 46 controls the direction and rotational speed of the motor 44 of the pump 10 via signal line 47. In this regard, the microprocessor 46 controls the pressure and direction of gas flow within the breathing circuit 8. The microprocessor 46 also has the ability to maintain a prescribed level of positive pressure with a patient's upper airway region when the device 2 is in the positive airway pressure mode. The microprocessor 46 also compensates for patient inhalation and exhalation during the positive airway pressure mode, which would otherwise alter the prescribed pressure. The microprocessor 46 thus controls the pump 10 to maintain the set pressure. The microprocessor 46 is preferably capable of delivering positive airway pressure in either CPAP or BiPAP mode.

As seen in FIGS. 4 and 5, The microprocessor 46 is further coupled to an input source 48 via signal line 49 and is used to change various operational parameters of the device 2 such as: positive airway pressure, ramp duration (the ramp feature is described in more detail below), ramp starting pressure, ramp rate, and calibration pressures. The microprocessor 46 is also coupled to an on/off/ramp switch 50 that toggles between an "on" position, an "off" position, and a "ramp" mode. Of course, the switch 50 may include only an "on" and "off" position without any "ramp" position. In addition, the switch 50 may be combined with IC switch 51.

The turbine 40 of the pump 10 is housed within a mixing chamber 52, as seen in FIG. 1, in the breathing circuit 8. The mixing chamber 52 serves to mix the patient's exhaled gases with atmospheric air used to dilute the exhaled gas during the indirect calorimetry mode.

An indirect calorimetry module 12 is also located within the breathing circuit 8. The indirect calorimetry module 12 is preferably located between the first end 18 of the breathing circuit 8 and the pump 10. The indirect calorimetry module 12 is used to measure parameters needed to measure the patient's REE. REE is generally measured in kilocalories/day. The indirect calorimetry module 12 preferably includes an oxygen sensor 56, a carbon dioxide sensor 58, and a flow sensor 60.

The oxygen sensor 56 is preferably fast-acting oxygen sensor 56 that exploits oxygen's high paramagnetic susceptibility. The oxygen sensor 56 is preferably a paramagnetic oxygen analyzer. Generally, a diamagnetic glass dumbbell made of borosilicate glass is suspended in a magnetic field. The glass dumbbell will attempt to rotate in proportion to the partial pressure of oxygen surrounding it. The glass dumbbell is preferably orientated horizontally and is supported by a rare metal taut-band suspension and null balanced by feedback current for increased natural frequency.

The carbon dioxide sensor 58 is preferably a rapid-response Non-Dispersive Infrared (NDIR) sensor. The NDIR carbon dioxide sensor 58 involves directing a beam of infrared light through a sample of gas and measuring the amount of infrared energy that is being absorbed. The carbon dioxide, sensor 58 can also be referred to as a thermopile detector. The carbon dioxide sensor 58 generally includes one or more thermopile deposition layers that are disposed adjacent to optical filters used to screen a discrete band or range of wavelengths.

Referring to FIG. 1, the flow sensor 60 preferably is an ultrasonic flow sensor 60. The ultrasonic flow sensor 60 operates by measurements are fast, reliable, and accurate. Measurement is independent of gas composition, pressure, temperature, and humidity. Transducers (not shown) are located on either side of the flow path to send and receive sound signals in alternating directions. When gas flow is present in the breathing circuit 8, a pulse of sound that travels against the direction of flow slows down, taking longer to reach the opposing transducer. A pulse that travels in the direction of flow moves faster and takes a shorter time to reach the opposing transducer. The transit time of the sound pulses is precisely measured with a digital clock. The digital clock is preferably incorporated into the microprocessor 46. Flowrate is then calculated from the two transit times. While an ultrasonic flow sensor 60 is preferred, other types of flow sensors can also be used to measure the flow rate.

The oxygen sensor 56, carbon dioxide sensor 58, and flow sensor 60 are preferably of the type and nature mentioned above. Certain of these components (such as the oxygen sensor 56 and the carbon dioxide sensor 58) are commercially available, for example, in SensorMedics Vmax series of diagnostic instruments available from SensorMedics Corporation, 22705 Savi Ranch Parkway, Yorba Linda, Calif. 92887-4645. It should be understood, however, that different types of sensors (oxygen, carbon dioxide, and flow) can also be used in the device 2 and should be considered to fall within the scope of the invention. For example, slower response sensors 56, 58 may be used if they provide accurate REE measurements.

Referring to FIG. 4, the oxygen sensor 56, the carbon dioxide sensor 58, and the flow sensor 60 are connected via signal lines 70, 71, and 73, respectively to the microprocessor 46. The sensors 56, 58 and 60 can be powered via a separate power line (not shown) or through the microprocessor 46. The device 2 also includes a display 72 for displaying the calculated REE. The display 72 is connected with the microprocessor 46 via signal line 74. The display 72 is preferably located on the external side of the housing 4, as shown in FIG. 3.

Referring to FIG. 2, the device 2 includes an air filter 76 positioned within the housing 6. The air filter 76 is advantageously positioned distal to the first end 18 of the breathing circuit 8. The air filter 76 filters contaminants such as dust, particulates, and the like from the breathing circuit 8. The air filter 76 is preferably removable from the housing 6 for periodic cleaning and replacement.

During use of the device 2 in the positive airway pressure mode, the pump 10 aspirates gas (room air) through the air filter 76 and into the breathing circuit 8 via the first end 18. An initial calibration step is performed where flow sensor 60 is calibrated to the pump 10 speed. In addition, the oxygen sensor 56 and the carbon dioxide sensor 58 are initially brought to zero reading and then calibrated to room air concentrations of the gases.

When the device 2 operates in the indirect calorimetry mode, the pump 10 reverses direction and the expired gases from the patient 4 are pumped into the indirect calorimetry module 12. The expired gases from the patient 4 are first diluted with atmospheric air. The atmospheric air used for dilution enters the breathing circuit 8 through the patient interface device 26, i.e., nasal face mask 30, via vents 34. The atmospheric air and expired gases are mixed within the breathing circuit 8 and in the mixing chamber 52. The mixture of gases then passes through the indirect calorimetry module 12 where oxygen concentration, carbon dioxide concentration, and flow rate are measured by the oxygen sensor 56, carbon dioxide sensor 58, and flow sensor 60, respectively. These values are reported to the microprocessor 46 where the information is stored and analyzed.

The indirect calorimetry method operates on the dilution principle. Generally, all of the patient's 4 expired gases are collected and diluted with a known flow (i.e., volume) of atmospheric (room) air. This dilution flow is usually about four times the patient's 4 normal minute ventilation (minute ventilation is the total volume of gas expired in one minute $V_E$(L/min)). The dilution flow rate is controlled by the speed of the pump 10 and the size and numbers of vents 34 in the nasal face mask 30. Since the size and number of vents 34 in the nasal facemask 30 is fixed, the speed of the pump 10 is used to control the dilution flow rate. The dilution flow rate for each patient 4 can be determined empirically or through estimation techniques using data derived from the pump 10 and the flow sensor 60.

Data from the sensors 56, 58, and 60 can be acquired on a realtime, near real-time, or periodic basis and reported to the microprocessor 46. Based on the data received from sensors 56, 58, and 60, the microprocessor 46 calculates minute ventilation $V_E$, oxygen consumption $VO_2$ (L/min), and carbon dioxide production $VCO_2$ (L/min). $V_E$ is preferably obtained through the following formula:

$$V_E = \text{tidal breath} \times \text{respiratory rate} \quad (1)$$

The patient's tidal breath and respiratory rate can be determined using the flow sensor 60 and/or pump 10, which can sense and report to the microprocessor 46 a patient's 4 inhalation and expiration. Alternatively, these variables can be determined empirically, and an average value is input via input source 48 to the microprocessor 46.

$VO_2$ is calculated with the following formula:

$$VO_2 = V_E(FIO_2 - FEO_2) \quad (2)$$

where $FIO_2$ is the fraction of oxygen in the inspired gas and $FEO_2$ is the fraction of oxygen in the expired gas of the patient 4.

$VCO_2$ is calculated with the following formula:

$$VCO_2 = V_E(FECO_2 - FICO_2) \quad (3)$$

where $FICO_2$ is the fraction of carbon dioxide in the inspired gas and $FECO_2$ is the fraction of carbon dioxide in the expired gas of the patient 4. The parameters $FIO_2$, $FEO_2$, $FICO_2$, and $FECO_2$ are calculated by the microprocessor 46 from data from sensors 56, 58, and 60.

From the preliminary calculations, the patient's REE is determined using the Weir equation where REE (Kcal/day)= 3.94($VO_2$)+1.1($VCO_2$)+1.44. The calculated REE is displayed on display 72. An alarm or the like may sound so that the patient 4 or other person may read the REE.

Generally, a patient 4 who is suspected of having OSA will usually have a diagnostic sleep examination consisting of a polygraphic recording of air flow, respiratory effort, blood oxygen saturation, body position, and length of sleep time. Often, other parameters, such as electroencephalography, will be recorded to determine the stages of sleep and amount of time the patient sleeps in each stage. From this data, diagnosis and prescription can be made. If various criteria indicate increased airway resistance and/or obstruction to air flow, the patient is placed on positive airway pressure (CPAP or BiPAP) during polygraphic recording.

Once it has been determined that a patient 4 will benefit from positive airway pressure, the level of pressure will be titrated during the polygraphic recording until the increased resistance and/or obstructive symptoms are resolved. The doctor or other authorized professional may program the device 2 with the settings required (i.e., pressure settings, ramp settings). The patient 4 then receives the device 2 for home use.

The patient 4 also receives a medically prescribed nutrition plan or program for weight reduction and/or weight control. The device 2 is used in conjunction with the prescribed program to objectively monitor the patient's weight reduction or control program. In its most general sense, the device 2 provides positive airway pressure to the patient 4 during periods of sleep while also performing periodic indirect calorimetry measurements of REE that are used to adjust the patient's diet. The REE value, which is displayed on the device 2, is used to control diet.

For patients using the device 2, a doctor or other qualified professional prescribes a diet to the patient having a total caloric value less than the amount of calories required for normal metabolic activity. The prescribed diet thus induces weight loss. The metabolic rate of a patient 4, however, varies from person to person. Even with respect to a single individual, the person's metabolic rate can vary from day-to-day. The device 2 provides a convenient way of monitoring a patient's metabolic rate through measurement of REE at any time.

For example, a normal healthy 250 lb. male might metabolize on the order of 2,500 calories per day. To reduce this person's weight to about 200 lbs., and thus reduce the adipose tissue in the hypopharynx to reduce OSA in the patient, a doctor or other professional might prescribe a diet of around 1,800 calories per day. A device 2 would also be prescribed to the patient 4 to (1) provide positive airway pressure to alleviate OSA symptoms, and (2) verify that the patient 4 is consuming only enough food to metabolize 1,800 calories each day.

At night time or prior to sleep, the patient dons the patient interface device 26, and preferably a nasal face mask 30. The device 2 is turned on using on/off/ramp switch 50. In the "on" position, the device 2 delivers a steady positive pressure to the patient. In the "ramp" position, the positive pressure starts at a low level and generally increases or ramps up to a final pressure as the night progresses. This feature is typically used when the patient 4 has difficulty falling asleep with the device 2 or the patient 4 is otherwise uncomfortable with the positive pressure delivered by the device 2.

When the patient 4 wakes up after a period of sleep, the patient 4 switches the device 2 into indirect calorimetry (IC) mode. In one aspect of the invention, the patient 4 switches the IC switch 51 (as seen in FIG. 5) to switch the device 2 into IC mode. In the IC mode, the pump 10 reverses and the indirect calorimetry module 12 is activated. The patient's 4 expired gases are then pumped through the breathing circuit 8 in a reverse direction. Measurements are taken by sensors 56, 58, and 60 and reported to the microprocessor 46. Measurements are taken for a period of about ten minutes to acquire data. The microprocessor calculates the REE and displays the value on the display 72.

In another, separate aspect of the invention, the device 2 automatically switches between a positive airway pressure mode and the IC mode. The microprocessor 46 utilizes an internal clock and switches between a positive airway pressure mode and an IC mode at set or random times during periods of sleep. If the IC times are set manually, the time can be input to the device 2 via input source 48. When the microprocessor 46 detects that it is time to switch, the pump 10 is slowed down until zero positive airway pressure is reached. At this point, the pump 10 reverses direction and pumps gases into the indirect calorimetry module 12. The IC mode may continue for several minutes such that an accurate REE measurement can be made. The calculated REE is then stored on the microprocessor 46, which can later be displayed on the display 72.

Preferably, the on/off/ramp switch 50, the IC switch 51, and the input source 48 are located on the underside of the device 2 as shown in FIG. 5. By positioning these features on the underside of the device 2, it is more difficult to accidentally switch the device 2 into a different mode. Of course, the placement of these components can be positioned on other portions of the device 2, including the top and sides.

Once the patient 4 has achieved the desired weight, the positive airway pressure is typically reduced to a lower pressure. In addition, the frequency of indirect calorimetry monitoring can also be reduced. These changes to the operational parameters can be.input to the microprocessor 46 via input source 48. Typically, a doctor or other health care provider makes the changes to the device 2.

While embodiments of the present invention have been shown and described, various modifications may be made without departing from the scope of the present invention. The invention, therefore, should not be limited, except to the following claims, and their equivalents.

What is claimed is:

1. A device for applying positive airway pressure to a patient and measuring the patient's resting energy expenditure, the device comprising:
   a breathing circuit having a first end and a second end;
   a patient interface device coupled to one of the first and second ends;
   a bi-directional pump positioned within the breathing circuit between the first end and the second end; and
   an indirect calorimetry module positioned within the breathing circuit, the indirect calorimetry module measuring the patient's resting energy expenditure.

2. A device according to claim 1, the breathing circuit further comprising a patient circuit.

3. A device according to claim 2, wherein the patient circuit comprises flexible tubing.

4. A device according to claim 1, the indirect calorimetry module comprising an oxygen sensor, a carbon dioxide sensor, and a flow sensor.

5. A device according to claim 4, the device comprising a microprocessor, the microprocessor calculating the patient's minute ventilation.

6. A device according to claim 5, the microprocessor calculating oxygen consumption ($VO_2$).

7. A device according to claim 6, the microprocessor calculating carbon dioxide production ($VCO_2$).

8. A device according to claim 7, the microprocessor calculating resting energy expenditure.

9. A device according to claim 8, the device comprising a display for displaying the resting energy expenditure.

10. A device according to claim 4, the device comprising a vent for introducing atmospheric air into the breathing circuit during patient exhalation.

11. A device according to claim 1, wherein the device is a continuous positive air pressure (CPAP) device.

12. A device according to claim 1, wherein the device is a bi-level positive airway pressure (BiPAP) device.

13. A method of supplying positive airway pressure to a patient comprising the steps of:
   supplying a patient with positive airway pressure via a breathing circuit, the positive airway pressure providing for a flow of gas traveling through the breathing circuit in a first direction;
   reversing in-line the flow of gas in the breathing circuit during one or more expiration breaths of a patient in a second direction;
   monitoring a concentration of oxygen and a concentration of carbon dioxide in the breathing circuit during the one or more expiration breaths;
   monitoring a flow rate of gas in the breathing circuit during the one or more expiration breaths; and
   calculating a resting energy expenditure of the patient based on the concentration of oxygen, the concentration of carbon dioxide, and the flow rate within the breathing circuit.

14. A method according to claim 13, the method comprising the step of displaying the resting energy expenditure of the patient.

15. A method according to claim 13, wherein the patient is supplied with constant positive airway pressure.

16. A method according to claim 13, wherein the patient is supplied with bi-level positive airway pressure.

17. A method of supplying positive airway pressure to a patient comprising the steps of:
   supplying a patient with positive airway pressure via a breathing circuit, the positive airway pressure providing for a flow of gas traveling through the breathing circuit in a first direction;
   reversing the flow of gas in the breathing circuit during one or more expiration breaths of a patient in a second direction; wherein the flow of gas is reversed automatically by a device;
   monitoring a concentration of oxygen and a concentration of carbon dioxide in the breathing circuit during the one or more expiration breaths;
   monitoring a flow rate of gas in the breathing circuit during the one or more expiration breaths; and
   calculating a resting energy expenditure of the patient based on the concentration of oxygen, the concentration of carbon dioxide, and the flow rate within the breathing circuit.

18. A method of supplying positive airway pressure to a patient comprising the steps of:
   supplying a patient with positive airway pressure via a breathing circuit, the positive airway pressure providing for a flow of gas traveling through the breathing circuit in a first direction;
   reversing the flow of gas in the breathing circuit during one or more expiration breaths of a patient in a second direction; wherein the flow of gas is reversed manually;
   monitoring a concentration of oxygen and a concentration of carbon dioxide in the breathing circuit during the one or more expiration breaths;
   monitoring a flow rate of gas in the breathing circuit during the one or more expiration breaths; and
   calculating a resting energy expenditure of the patient based on the concentration of oxygen, the concentration of carbon dioxide, and the flow rate within the breathing circuit.

19. A method of supplying positive airway pressure to a patient comprising the steps of:
   supplying a patient with positive airway pressure via a breathing circuit, the positive airway pressure providing for a flow of gas traveling through the breathing circuit in a first direction;
   reversing the flow of gas in the breathing circuit during one or more expiration breaths of a patient in a second direction; wherein the flow of gas is reversed randomly;
   monitoring a concentration of oxygen and a concentration of carbon dioxide in the breathing circuit during the one or more expiration breaths;
   monitoring a flow rate of gas in the breathing circuit during the one or more expiration breaths; and
   calculating a resting energy expenditure of the patient based on the concentration of oxygen, the concentration of carbon dioxide, and the flow rate within the breathing circuit.

20. A device for applying positive airway pressure to a patient and measuring the patient's resting energy expenditure, the device comprising:
   a breathing circuit, the breathing circuit having a patient interface device connected at one end and an inlet/exhaust port at the other end of the breathing circuit;
   bi-directional pump positioned within the breathing circuit between the patient interface device and the inlet/exhaust port;
   an indirect calorimetry module positioned within the breathing circuit and adjacent to the bi-directional pump, the indirect calorimetry module comprising an oxygen sensor, a carbon dioxide sensor, and a flow rate sensor; and
   a microprocessor for calculating the patient's resting energy expenditure based on a concentration of oxygen, a concentration or carbon dioxide, and a flow rate within breathing circuit.

* * * * *